US008598338B2

(12) United States Patent
Bair et al.

(10) Patent No.: US 8,598,338 B2
(45) Date of Patent: Dec. 3, 2013

(54) COMPOSITIONS AND METHODS FOR USING A SOLID SUPPORT TO PURIFY DNA (75) Inventors: Robert Jackson Bair, Plymouth, MN (US); Kristen Campbell Benedict, Maple Grove, MN (US); Wendy J. Kivens, Edina, MN (US); Robert W. Kwiatkowski, Jr., Verona, WI (US); Kim Paulsen, Brooklyn Park, MN (US); Daniel A. Strom, Minneapolis, MN (US); John M. Wages, Tupelo, MS (US)

(73) Assignee: QIAGEN North American Holdings, Inc., Germantown, MD (US)

( * ) Notice: Subject to any disclaimer, the term of this patent is extended or adjusted under 35 U.S.C. 154(b) by 367 days.

(21) Appl. No.: 12/718,713

(22) Filed: Mar. 5, 2010

(65) Prior Publication Data

US 2010/0160619 A1 Jun. 24, 2010

Related U.S. Application Data (60) Division of application No. 10/909,724, filed on Aug. 2, 2004, now abandoned, which is a continuation-in-part of application No. 10/418,194, filed on Apr. 16, 2003, now Pat. No. 7,148,343, which is a continuation-in-part of application No. 09/974,798, filed on Oct. 12, 2001, now Pat. No. 7,893,228.

(51) Int. Cl.
C07H 21/04 (2006.01)

(52) U.S. Cl.
CPC ..................... C07H 21/04 (2013.01)
USPC ........................ 536/127; 536/25.4; 536/25.42

(58) Field of Classification Search
None
See application file for complete search history.

(56) References Cited

U.S. PATENT DOCUMENTS

| | | |
|---|---|---|
| 41,332 A | 1/1864 | Washburn |
| 4,483,920 A | 11/1984 | Gillespie et al. ............... 351/722 |
| 4,843,155 A | 6/1989 | Chomczynski ................ 536/27 |
| 5,010,183 A | 4/1991 | Macfarlane ................... 536/27 |
| 5,057,426 A | 10/1991 | Henco et al. ................... 435/270 |
| 5,132,207 A | 7/1992 | Kohne et al. ..................... 435/6 |
| 5,155,018 A | 10/1992 | Gillespie et al. ............... 435/91 |
| 5,234,809 A | 8/1993 | Boom et al. .................... 435/91 |
| 5,346,994 A | 9/1994 | Chomczynski ................ 530/419 |
| 5,405,951 A | 4/1995 | Woodard ................... 536/25.41 |
| 5,580,970 A * | 12/1996 | Hendricks et al. .......... 536/24.32 |
| 5,599,667 A | 2/1997 | Arnold, Jr. et al. ............... 435/6 |
| 5,637,687 A | 6/1997 | Wiggins ....................... 536/25.4 |
| 5,728,822 A | 3/1998 | Macfarlane ................. 536/25.41 |
| 5,939,259 A | 8/1999 | Harvey et al. ..................... 435/6 |
| 5,945,515 A | 8/1999 | Chomczynski ............... 530/412 |
| 5,958,677 A | 9/1999 | Lee et al. ........................... 435/5 |
| 5,972,613 A | 10/1999 | Somack et al. ................... 435/6 |
| 5,973,137 A | 10/1999 | Heath .......................... 536/25.4 |
| 5,985,572 A | 11/1999 | Macfarlane ...................... 435/6 |
| 5,990,302 A | 11/1999 | Kuroita et al. ................ 536/25.4 |
| 6,037,465 A | 3/2000 | Hillebrand et al. ........ 536/25.42 |
| 6,204,375 B1 | 3/2001 | Lader .......................... 536/25.4 |
| 6,218,531 B1 | 4/2001 | Ekenberg .................... 536/25.41 |
| 6,465,639 B1 | 10/2002 | van Gemen et al. ......... 536/25.4 |
| 6,503,716 B1 | 1/2003 | Lai et al. ........................... 435/6 |
| 6,528,641 B2 | 3/2003 | Lader .......................... 536/25.4 |
| 6,617,170 B2 | 9/2003 | Augello et al. ............... 436/176 |
| 6,699,987 B2 | 3/2004 | Hillebrand et al. .......... 536/25.4 |
| 6,855,499 B1 | 2/2005 | Nargessi ........................... 435/6 |
| 7,115,719 B2 | 10/2006 | Paulsen ......................... 530/427 |
| 7,148,343 B2 | 12/2006 | Bair, Jr. et al. ............... 536/25.4 |
| 2001/0041332 A1 | 11/2001 | Hillebrand et al. ............... 435/6 |
| 2002/0001812 A1 | 1/2002 | Smith et al. ....................... 435/6 |
| 2002/0106686 A1 | 8/2002 | McKernan ........................ 435/6 |
| 2002/0127587 A1 | 9/2002 | Simms et al. ..................... 435/6 |
| 2003/0073830 A1 | 4/2003 | Heath et al. .................. 536/25.4 |
| 2003/0092045 A1 | 5/2003 | Nargessi et al. .................. 435/6 |
| 2003/0106107 A1 | 6/2003 | Shinozaki et al. ............. 800/289 |
| 2004/0019196 A1 | 1/2004 | Bair, Jr. et al. ............... 536/25.4 |
| 2004/0245163 A1 | 12/2004 | Lim et al. .................... 210/323.1 |
| 2005/0032105 A1 | 2/2005 | Bair et al. ......................... 435/6 |
| 2005/0191760 A1 | 9/2005 | Heath et al. .................. 436/177 |
| 2006/0105372 A1 | 5/2006 | Bair et al. ......................... 435/6 |
| 2007/0043216 A1 | 2/2007 | Bair, Jr. et al. ............... 536/25.4 |
| 2007/0092403 A1 | 4/2007 | Wirbisky et al. ................ 422/65 |

FOREIGN PATENT DOCUMENTS

| | | |
|---|---|---|
| EP | 0818461 | 1/1998 |
| JP | 9-327290 A | 12/1997 |
| JP | 2002-187897 A | 7/2002 |
| WO | 92/07863 | 5/1992 |
| WO | 95/01359 | 1/1995 |
| WO | 95/02049 | 1/1995 |
| WO | WO 95/21849 A1 | 8/1995 |

(Continued)

OTHER PUBLICATIONS

Ahmad, F., "Free Energy Changes in Ribonuclease A Denaturation," *The Journal of Biological Chemistry*, 258 (18): 11143-11146, 1983.
Ahmad, F., "Free Energy Changes in Denaturation of Ribonuclease a by Mixed Denaturants," *The Journal of Biological Chemistry*, 259 (7): 4183-4186, 1984.
Bugos et al., "RNA isolation from plant tissues recalcitrant to extraction in guanidine," *BioTechniques*, 19: 734-737, 1995.
Chomczynski et al., "Single-step method of RNA isolation by acid guanidinium thiocyanate-phenol-chloroform extraction," *Analytical Biochemistry*, 162: 156-159, 1987.
Collins, K. D., "Sticky ions in biological systems," *Proceedings of the National Academy of Sciences of the USA*, 92: 5553-5557, 1995.
Cox et al., "A single-stop procedure for the isolation of individual mRNA species from crude lysates of Physarum polycephalum," *FEBS Letters*, 155: 73-80, 1983.

(Continued)

*Primary Examiner* — Eric S Olson
(74) *Attorney, Agent, or Firm* — Seed IP Law Group PLLC (57) ABSTRACT

The present disclosure provides methods for isolating substantially pure and undegraded DNA from biological material via a solid support. The methods may use a DNA lysing solution that comprises a surfactant, a DNA-complexing salt (e.g., a lithium salt), and a buffer. Alternatively, the methods may use a solid support pre-treated with the DNA lysing solution.

38 Claims, 2 Drawing Sheets

(56) References Cited

FOREIGN PATENT DOCUMENTS

| WO | 95/34569 | 12/1995 |
|---|---|---|
| WO | 96/18731 | 6/1996 |
| WO | 99/39009 | 8/1999 |
| WO | 03/033739 | 4/2003 |
| WO | 2004/094635 | 11/2004 |

OTHER PUBLICATIONS

*CRC Handbook of Chemistry and Physics*, 62$^{nd}$ Edition. CRC Press, Boca Raton, Florida, (1981-1982), D-96, B-75, B-91, B-113, B-132, B-147.

Dahle et al., "Isolation of RNA from Cells in Culture Using Catrimox-14™ Cationic Surfactant," *BioTechniques*, 15 (6): 1102-1105, 1993.

Galinski et al., "The Kosmotropic (structure forming) Effect of Compensatory Solutes," *Comparative Biochemistry and Physiology, 117 Part A: Physiology* (3): 356-365, 1997.

Hofmeister, "On the Theory of the Effects of Salts," *Arch. Exp. Pathol. Pharmakol.*, 24: 247-260, 1888.

Jobes et al., "Plant DNA Isolation: A Method to Efficiently Remove Polyphenolics, Polysaccharides, and RNA," *Taxon*, 44 (3): 379-386, 1995.

Kazakov, S. A., *Bioorganic Chemistry: Nucleic Acids*, Oxford University Press, New York, 1996, Chapter 9, "Nucleic Acid Binding and Catalysis by Metal Ions," 244-477.

Kondo et al., "Rapid isolation of plasmid DNA by LiCl-ethidium bromide treatment and gel filtration," *Analytical Biochemistry*, 198 (1): 30-35, 1991.

Kosmotropes and Chaotropes, URL = http://www.lsbu.ac.uk/water/kosmos.html, download date Aug. 18, 2004.

Krawetz et al., "Isolation and fractionation of total nucleic acids from tissues and cells," *Journal of Biochemical and Biophysical Methods*, 12: 29-36, 1986.

Lemarchand et al., "Optimization of microbial DNA extraction and purification from raw wastewater samples for downstream pathogen detection by microarrays," *Journal of Microbiological Methods*, 63 (2): 115-126, 2005.

Lever et al., "Some ways of looking at compensatory kosmotropes and different water environments," *Comparative Biochemistry and Physiology. Part A, Molecular & Integrative Physiology*, 130 (3): 471-486, 2001.

Macfarlane et al., "Isolating RNA from clinical samples with Catrimox-14 and lithium choloride," *Journal of Clinical Laboratory Analysis*, 11 (3): 132-139, 1997.

Sambrook et al., *Molecular Cloning: A Laboratory Manual*, vol. 3, 2$^{nd}$ Edition, Cold Spring Harbor Laboratory Press, 1989, "Concentrating Nucleic Acids: Precipitation with Ethanol or Isopropanol," E10 & E15.

Surzycki et al., "General Aspects of DNA Isolation and Purification," Springer-Verlag GMBH and Co. KG, Berlin, 1-32, 2000.

Technical Bulletin #160: The Use of LiCl Precipitation for RNA Purification, URL = http://www.abmbion.com/techlib/tb/tb__160, html, downloaded 2003.

Washabaugh et al., "The systematic characterization by aqueous column chromatography f solutes which affect protein stability," *The Journal of Biological Chemistry 261* (27): 12477-12485, 1986.

Wiggins, P. M., "High and low density intracellular water," *Cellular and Molecular Biology*, 47 (5): 735-744, 2001.

Witchel et al., "Milligram quantity preparation of RNA from a marine invertebrate with a high fluid content," *Biotechniques*, 21 (6): 1024-1026, 1996.

\* cited by examiner

Figure 1: % of Theoretical DNA Yield Comparison
QIAamp Blood DNA Midi Kit vs. Versagene Blood DNA Kit Means and Standard Deviations

| Level | Number | Mean | Std Dev | Std Err Mean |
|---|---|---|---|---|
| QIAamp DNA Midi | 4 | 30.28 | 14.19 | 7.10 |
| Versagene DNA | 4 | 53.28 | 16.66 | 8.33 |

Figure 2: % of Theoretical DNA Yield by Lysis LiCl Concentration and pH

Means and Standard Deviations

| Level | Number | Mean | Std Dev | Std Err Mean |
|---|---|---|---|---|
| 6 M LiCl pH 8 | 3 | 58.98 | 17.35 | 10.02 |
| 6 M LiCl pH 9 | 3 | 70.34 | 7.60 | 4.39 |
| 8 M LiCl pH 8 | 3 | 67.20 | 11.07 | 6.39 |

COMPOSITIONS AND METHODS FOR USING A SOLID SUPPORT TO PURIFY DNA

CROSS-REFERENCE TO RELATED APPLICATIONS

This application is a divisional application of U.S. Ser. No. 10/909,724, filed Aug. 2, 2004, which is a continuation-in-part of U.S. application Ser. No. 10/418,194, filed Apr. 16, 2003, which is a continuation-in-part of U.S. application Ser. No. 09/974,798, filed Oct. 12, 2001, which applications are incorporated by reference herein.

STATEMENT REGARDING FEDERALLY SPONSORED RESEARCH OR DEVELOPMENT

Work relating to this application was supported by National Institutes of Health Grant 1 R43 CA106124-01. The government may have certain rights in the invention.

BACKGROUND OF THE INVENTION

Nucleic acids such as deoxyribonucleic acid (DNA) and ribonucleic acid (RNA) are used extensively in the field of molecular biology for research and clinical analyses. There are numerous nucleic acid purification methods that fall into two general categories, liquid phase and solid phase purification. In liquid phase purification, the DNA remains in the liquid phase while impurities are removed by precipitation and/or centrifugation. In solid phase purification, the DNA is bound to a solid support while impurities are selectively eluted. Conventional liquid phase and solid phase purification strategies require many steps and hazardous reagents.

SUMMARY OF THE INVENTION

The present invention provides a formulation for isolating and/or purifying nucleic acids. The formulation contains a lithium salt at a concentration of at least about 1 M, at least one surfactant, and a buffer. The formulation may further contain a chelating agent, such as EDTA or citrate. The formulation of the present invention may lack a chaotrope and/or a strong chaotropic substance. Examples of strong chaotropic substances are guanidinium salts, urea, ammonium, cesium, rubidium, potassium, or iodide salt. The lithium salt present in the formulation may be lithium chloride. The lithium salt may be present at a concentration of 2 M to 10 M, or at a concentration of 2 M to 6 M. In certain embodiments, the concentration of the lithium salt may be at 2 M, 3 M, 4 M, 5 M, 6 M, 7 M, 8 M, 9 M or 10 M, or any range between (such as 5.5 M). The formulation may have a pH of above about 7, such as between about 7 and about 9 (e.g., a pH of about 8, about 8.5, or about 9). In certain embodiments, the nucleic acid that is isolated and/or purified is DNA.

The surfactant of the present formulation may be present at a concentration of about 10% to about 40% (or any percentage in between) of the total volume of the formulation. The surfactant or surfactants in the formulation of the present invention may be a detergent. The detergent may be an anionic, cationic, zwitterionic or non-ionic detergent. In one embodiment, the surfactant is a non-ionic detergent. Examples of appropriate non-ionic detergents include a Tween, Triton, Nonidet, Igepal or Tergitol. For instance the detergent may be Triton-X.

Further, the surfactant may be diethyl glycol monoethyl ether (DGME). The DGME may be present at a concentration of about 5% to about 35% (or any percentage in between) of the total volume of the formulation. In general, as the concentration of other components of the formulation increase, the amount of DGME is increased so as to increase the solubility of the other components. In certain embodiments, the surfactant is a mixture of Triton-X and DGME. In one embodiment the surfactant is a mixture of 5% v/v Triton-X and 5% v/v DGME. In one embodiment, the surfactant is present at a concentration of about 10% v/v of the final volume of the solution.

In one embodiment, the surfactant is an anionic detergent. Examples of appropriate detergents include sodium dodecyl sulfate (SDS) or N-lauroyl sarcosine. In one embodiment, SDS is the anionic detergent. In one embodiment, the detergent is be present at a concentration of between about 0.05-0.2% (or any percentage in between).

In one embodiment the concentration is about 0.1%.

In certain embodiments, the formulation contains a mixture of more than one surfactant at a concentration of 0.1% SDS and 30% DGME.

The buffer of the formulation of the present invention may have a pKa of at least about 8. The chelating agent may be EDTA or citrate.

In one embodiment of the present invention the formulation for isolating and purifying nucleic acids contains a lithium salt at a concentration of at least about 1 M, a surfactant, a buffer, and an optional chelating agent, wherein the solution has pH of above about 7.

In another embodiment of the present invention, the formulation for isolating and purifying nucleic acids consists essentially of a lithium salt at a concentration of at least about 1 M, at least one surfactant, a buffer, and an optional chelating agent.

In yet another embodiment, the formulation of the present invention consists essentially of a lithium salt, at least one surfactant, a buffer, and an optional chelating agent, wherein the solution has pH of above about 7.

A further embodiment of the present invention consists essentially of a lithium salt at a concentration of at least about 1 M, a surfactant, a buffer, and an optional chelating agent, wherein the solution has pH of above about 7.

The present invention also provides methods for purifying substantially pure and undegraded DNA from biological material. The biological material used in the method of the present invention may be a crude sample or a partially purified mixture of nucleic acids. Examples of biological materials include a sample of eukaryotic cells, prokaryotic cells, microbial cells, bacterial cells, plant cells, mycoplasma, protozoa, bacteria, fungi, virus, yeast, or rickettsia, or homogenates thereof. Additional examples of biological materials include whole blood, bone marrow, cervical swabs, blood spot, blood serum, blood plasma, buffy coat preparation, saliva, cerebrospinal fluid, or solid animal tissue. Further examples of biological materials include feces, urine, tears, or sweat. The biological material may also be an environmental sample taken from air, water, sediment or soil. The biological material may be of a variety of sample types including, for example, cultured cells, fixed cells, and/or tissues. In one embodiment, the biological sample is a cervical cell sample. In another embodiment the biological sample is whole blood.

The solid support used in the methods of the present invention include components of silica, cellulose, cellulose acetate, nitrocellulose, nylon, polyester, polyethersulfone, polyolefin, or polyvinylidene fluoride, or combinations thereof. The solid support may be contained in a vessel, wherein the vessel is a centrifuge tube, spin tube, syringes, cartridge, chamber, multiple-well plate, or test tube, or combinations thereof. The solid support may be pre-treated with RNase solution prior to contacting the biological material with the solid support.

The lithium salt of the DNA Lysing Solution used in the method of the present invention is a DNA-complexing salt. Examples of lithium salts that may be used include lithium chloride or lithium bromide. The DNA-complexing salt of the DNA Lysing Solution may be present at a concentration greater than about 1 M. In one embodiment, the DNA-complexing salt may be present at a concentration of between 2 M and 8 M. In certain embodiments, the concentration of the DNA-complexing salt is at a concentration of about 2 M, 3 M, 4 M, 5 M, 6 M, 7 M, or 8 M, or any concentration in between (such as at about 5.5 M).

The Lysing Solution may optionally contain a chelating agent, such as EDTA or citrate.

The present invention provides a method involving the steps of contacting a biological material with a DNA Lysing Solution to form a mixture, wherein the DNA Lysing Solution is buffered at pH of greater than 7, and wherein the DNA Lysing Solution contains a lithium salt and at least one surfactant; contacting the mixture with a DNA Spiking Solution; contacting the mixture to a solid support such that DNA present in the biological material binds to the solid support; washing the solid support with a wash solution to remove biological materials other than bound substantially undegraded DNA; and eluting the DNA with a DNA Elution Solution in order to obtain substantially pure and undegraded DNA. "Substantially undegraded DNA binds to the solid support" means that the substantially undegraded DNA binds to the solid support while other cellular or non-cellular components found in the biological sample (such as cellular membranes or proteins) largely do not bind to the solid support.

The present invention provides a method for purifying substantially pure and undegraded DNA from biological material, involving the steps of contacting a biological material containing DNA with a solid support pre-treated with an DNA Lysing Solution, wherein the DNA Lysing Solution is buffered at a pH of greater than about 7, and wherein the DNA Lysing Solution contains a surfactant and a lithium salt; adding a DNA Spiking Solution to the biological material; contacting the biological material to the solid support in order to release nucleic acids comprising substantially undegraded DNA and non-nucleic acid biological matter, wherein the nucleic acids comprising substantially undegraded DNA bind to the solid support; washing the solid support with a Wash Solution to remove biological materials other than bound nucleic acids comprising undegraded DNA; and eluting the bound undegraded DNA from the solid support with an DNA Elution Solution. The Wash Solution may be buffered at a pH of greater than about 7. In certain embodiments the Wash Solution may be buffered between about 7 and about 9 (e.g., a pH of about 8, about 8.5, or about 9). The Lysing and/or Wash Solution used in the methods of the present invention formulation of the present invention may lack a chaotrope and/or a strong chaotropic substance.

The DNA Spiking Solution used in the methods of the present invention may be an alcohol. The alcohol may be isopropanol, ethanol, methanol or the like. The alcohol may be a mixture of alcohols. In one embodiment, the DNA Spiking Solution is 100% isopropanol.

The surfactant used in the methods of the present invention may be a detergent. The detergent may be a non-ionic detergent, such as a Tween, Triton, Nonidet, Igepal or Tergitol. The detergent may be an anionic detergent, such as SDS (sodium dodecyl sulfate) or N-lauroyl sarcosine. The surfactant may be a mixture of detergents, or a mixture of detergents with a solubilizing surfactant such as DGME.

The DNA Spiking Solution may contain an alkali-metal salt, such as lithium salt. The DNA Spiking Solution may be buffered at a pH greater than 7. In certain embodiments the DNA Spiking Solution may be buffered at a value between about 7 and about 9 (e.g., a pH of about 8, about 8.5, or about 9). The DNA Spiking Solution may contain a surfactant. In one embodiment, the surfactant is DGME.

The present invention further provides a method for purifying substantially pure and undegraded DNA from biological material, involving the steps of (a) contacting a biological material containing DNA with a solid support pre-treated with a DNA Lysing Solution buffered at a pH of greater than about 7 such that the DNA Lysing Solution is bound to the solid support, wherein the DNA Binding Solution contains a DNA-complexing salt; (b) adding an optional DNA Spiking Solution to the mixture; (c) contacting the biological material to the solid support such that nucleic acids comprising substantially undegraded DNA bind to the solid support; (d) washing the solid support with a DNA wash solution to remove biological materials other than bound nucleic acids comprising substantially undegraded DNA; and (e) preferentially eluting the bound substantially undegraded DNA from the solid support with an DNA Elution Solution in order to obtain substantially pure and undegraded DNA.

The present invention further provides a method for purifying substantially pure and undegraded DNA from biological material, involving the steps of (a) contacting a biological material containing DNA with a solid support pre-treated with a DNA Lysing Solution buffered at a pH of greater than about 7 such that the DNA Lysing Solution is bound to the solid support, the DNA Lysing Solution containing a surfactant and an DNA-complexing salt; (b) adding to the biological sample an optional DNA Spiking Solution; (c) contacting the biological material to the solid support in order to release nucleic acids comprising substantially undegraded DNA and non-nucleic acid biological matter, causing nucleic acids comprising substantially undegraded DNA to bind to the solid support; (d) washing the solid support with to remove biological materials other than bound nucleic acids comprising undegraded DNA; and (e) preferentially eluting the bound undegraded DNA from the solid support with an DNA Elution Solution in order to obtain substantially pure and undegraded DNA.

The present invention further provides a direct lysis method for purifying substantially pure and undegraded DNA from biological material, for instance whole blood, without using a red blood cell (RBC) lysis step, involving the steps of contacting a biological material containing DNA with a first DNA Lysing Solution, wherein the first DNA Lysing Solution is buffered at a pH of greater than about 7 and contains a surfactant at a concentration of between about 5-15% v/v and a DNA-complexing salt at a concentration of greater than 1 M, contacting the biological material with a second DNA Lysing Solution, wherein the second DNA Lysing Solution comprises a surfactant and a DNA-complexing salt greater than 1 M; contacting the mixture with a DNA Spiking Solution; contacting the mixture with a solid support, wherein nucleic acids comprising substantially undegraded DNA from the biological material bind to the solid support; washing the solid support with a DNA Wash Solution to remove biological materials other than bound nucleic acids comprising substantially undegraded DNA, the DNA Wash Solution containing a DNA-complexing salt and a surfactant; and preferentially eluting the bound substantially undegraded DNA from the solid support with an DNA Elution Solution. In certain embodiments, the second DNA Lysing Solution is buffered at a pH of greater than about 7. In certain embodiments, the concentration of the surfactant in the second DNA Lysing Solution is between about 25-35% v/v. In certain embodiments, the second DNA Lysing Solution also contains a chelating agent.

The present invention further provides a method for purifying substantially pure and undegraded DNA from biological material, for instance fixed cervical cell samples, involving the steps of contacting a biological material containing DNA with DNA Lysing Solution buffered at a pH of greater than about 7, the DNA Lysing Solution containing a surfactant and a DNA-complexing salt of greater than 1 M; adding to the mixture, an optional DNA Spiking Solution containing alcohol; contacting the biological material to the solid support in order to release nucleic acids comprising substantially undegraded DNA and non-nucleic acid biological matter, causing nucleic acids comprising substantially undegraded DNA to bind to the solid support; washing the solid support with a DNA Wash Solution to remove biological materials other than bound nucleic acids comprising undegraded DNA; and preferentially eluting the bound undegraded DNA from the solid support with a DNA Elution Solution in order to obtain substantially pure and undegraded DNA. In certain embodiments, the concentration of the surfactant in the DNA Lysing Solution is between about 25-35% v/v. In certain embodiments, the DNA Lysing Solution also contains a chelating agent.

As used herein, "substantially pure" means substantially free of RNA, carbohydrate, protein, lipid impurities, such that the DNA can be used in subsequent analyses known to those with skill in the art such as nucleic acid quantification, restriction enzyme digestion, DNA sequencing, hybridization technologies, such as Southern Blotting, etc., and amplification methods such as Polymerase Chain Reaction (PCR), Ligase Chain Reaction (LCR), Nucleic Acid Sequence Based Amplification (NASBA), Self-sustained Sequence Replication (SSR or 3SR), Strand Displacement Amplification (SDA), and Transcription Mediated Amplification (TMA), Quantitative PCR (qPCR), or other DNA analyses.

As used herein, "substantially undegraded" DNA means nondigested or intact DNA, which can be readily determined by one of skill in the art using standard techniques. "Substantially undegraded" DNA is not damaged by enzymatic, physical or chemical means during the purification methods of the present invention.

The reagents, methods and kits of the present invention may be used to isolate substantially pure and undegraded DNA over a wide range of biological sources, and life forms, all of which can be recovered over a wide molecular weight range. The substantially pure and undegraded DNA obtained from practicing the invention can be evaluated for purity, yield, size, reverse transcriptase or other hybridization processes, amplification, hybridization ability, etc. The biological samples include, for example, cell or viral suspensions and pellets thereof, body fluids, cervical cell swabs and tissue homogenates, etc. If the biological sample consists of cells or viruses, the cells or viruses may be enumerated. The enumeration may be conducted using standard cell counting methods such as an electronic cell counter (e.g., CBC5 Coulter Counter, Coulter Corp., Hialeah, Fla.) or a visual counting chamber (e.g., a hemacytometer, Bright Line, American Optical, Buffalo, N.Y.).

It should be noted that the indefinite articles "a" and "an" and the definite article "the" are used in the present application, as is common in patent applications, to mean one or more unless the context clearly dictates otherwise. Further, the term "or" is used in the present application, as is common in patent applications, to mean the disjunctive "or" or the conjunctive "and."

DETAILED DESCRIPTION

The use of chaotropic salts for the binding and purification of nucleic acids is well known in the art. For example, Kuroita et al. (U.S. Pat. No. 5,990,302) disclose that biological material may be lysed in an acidic solution containing a lithium salt and a chaotropic agent such as guanidinium isothiocyanate (GITC), after which the RNA is brought into contact with a nucleic acid-binding carrier such as silica. The RNA is subsequently purified by eluting from the silica in a low ionic-strength buffer. This method is disadvantageous in its use of hazardous substances such as the chaotropic salt, guanidine isothiocyanate.

Combinations of chaotropic substances such as guanidine isothiocyanate, guanidine hydrochloride, sodium iodide, and urea mixtures at ionic strengths greater than 4 M in conjunction with silica-based carriers have been taught in the art for RNA purification. For example, Hillebrand et al. (WO 95/34569) describes a one-step method involving a slurry of silica beads to which chaotropic substances are added in order to cause RNA to bind.

The apparent opposite approach to the use of chaotropes is the use of antichaotropes (also known as "kosmotropes" in the art) to isolate RNA. Hillebrand et al., (US 2001/0041332) describes the use of "antichaotropes," such as ammonium chloride (also cesium, sodium and/or potassium salts are mentioned), in combination with PVP (polyvinyl pyrrolidone) to lyse the starting sample and bind to the solid support with a detergent/alcohol mixture. Besides the fact that it is generally known that cesium and potassium are clearly considered to be chaotropes, due to their low charge density and weak hydration characteristics, while ammonium is considered to be a marginal chaotrope (Collins, K. Sticky Ions in Biological Systems, *Proc. Natl. Acad. Sci. USA,* 92 (1995), 5553-5557; Wiggins, P. M. High and Low Density Intracellular Water, *Cellular and Molecular Biology* 47 (5), 735-744), several disadvantages to the methods of Hillebrand exist. First, the methods use PVP, which has been investigated as a tumorigen. Secondly, heating steps of 65-70° C. are required for lysis and elution. Such heating may cause damage to the nucleic acids by nonspecific degradation or digestion resulting in limited downstream applications, such as incompatibility with restriction digests or blot analysis.

It should be noted that the method of selectively precipitating nucleic acids from a solution containing nucleic acids and other biological materials is physically different than that of using a solid phase to selectively bind the DNA or RNA molecules in a solution. A "precipitation" event is the reverse of a "solution" event. Solution involves the dissolving of a solute, such as DNA, by separation of that solute into molecules that are surrounded by solvent. Precipitation involves the removal of solvent and coalescence of individual DNA molecules into a solid that separates from the solvent. These Precipitation and Solution events occur within a solution environment and do not depend upon a separate and distinct solid phase on which DNA purification and separation occurs.

To advance the field of DNA sample preparation there is a need for solid phase DNA purification strategies. There is also a need for reagents and methods that are adaptable to solid phase purification strategies and are not only simple and rapid but also general in scope to maximize adaptability for automation. There is a need for reagents that are of generally low concentration, stable at room temperature (i.e., 20-25° C.), less hazardous (i.e., less corrosive, flammable or toxic), non-particulate to eliminate the need for mixing, and protective of DNA quality. There is also a need for methods with few steps that can be performed using a variety of biological starting materials, whether hydrated or dried, especially as applied to routine testing as found in clinical laboratories. The reagents must not inhibit subsequent DNA analysis procedures by interfering with the buffering capacity of PCR buffers, or cause degradation of polymerase, primers or oligonucleotides used in DNA amplification. There is also a need for methods with few steps that can be performed using a variety of biological starting materials, whether hydrated or dried, especially as applied to routine testing as found in clinical laboratories. The reagents and methods used in the solid phase purification strategy must also not interfere with standard experimental and/or diagnostic methods of nucleic acid manipulation.

Additionally, isolating and purifying nucleic acids has become more challenging with the discovery of more challenging sample types. For example, isolating and purifying DNA from cervical cells for use in molecular-based tests for HPV (human papilloma virus) have been rapidly adopted in clinical laboratories as the role of HPV infection in cervical cancer has become evident. Molecular diagnostic labs now perform over 6 million HPV diagnostic tests per year. However, preparation of DNA from cervical samples for molecular testing has not kept pace with the growing demand. In standard practice, the exfoliated cervical epithelial cells are harvested in a liquid media containing preservative, such as SurePath™ Preservative Fluid (TriPath Imaging, Burlington, N.C.) or the ThinPrep® Pap Test™ (Cytyc, Boxborough, Mass.), and the samples are often heavily contaminated with a variety of cellular and non-cellular components making isolation and purification a challenge. These contaminants can include mucus, white blood cells, red blood cells, and proteins. The current manual DNA purification methods have several significant disadvantages that impede further adoption of molecular-based HPV diagnostics in the clinical laboratory. There is now an urgent need for more efficient and effective methods for the purification of DNA from samples containing exfoliated cervical cells.

The present invention provides reagents, methods, and kits that incorporate a solid support for isolating substantially pure and undegraded DNA from fresh, frozen, and dried biological samples. The purified DNA is suitable for use in widely used analytical and diagnostic methods such nucleic acid quantification, restriction enzyme digestion, DNA sequencing, hybridization technologies, such as Southern Blotting, etc., and amplification methods such as Polymerase Chain Reaction (PCR), Ligase Chain Reaction (LCR), Nucleic Acid Sequence Based Amplification (NASBA), Self-sustained Sequence Replication (SSR or 3SR), Strand Displacement Amplification (SDA), and Transcription Mediated Amplification (TMA), Quantitative PCR (qPCR), or other DNA analyses.

Biological Materials and/or Samples

The present invention provides reagents, methods and kits for purifying DNA from biological samples. Such biological samples include biological material, typically in an aqueous mixture or dried, that contains DNA, including complex biological mixtures of prokaryotic or eukaryotic cells. Typically, the biological material also contains DNA, carbohydrates, proteins, and lipids. Biological materials include, but are not restricted to the following: body fluids such as whole blood, bone marrow, blood spots, blood serum, blood plasma, buffy coat preparations, saliva and cerebrospinal fluid, buccal swabs, cultured cells, fixed cells, cervical cell swabs, cell suspensions of bacteria or tissue homogenates, solid animal tissues such as heart, liver and brain, body waste products, such as feces and urine, environmental samples taken from air, water, sediment or soil, plant tissues, yeasts, bacteria, viruses, mycoplasmas, fungi, protozoa, rickettsia, and other small microbial cells. Lysates, homogenates, or partially purified samples of these biological materials may also be used. In one embodiment, the biological material is crude or partially purified mixtures of nucleic acids.

Reagents of the Present Invention

The present invention discloses four categories of reagents. These are DNA Lysing Solutions, DNA Spiking Solutions, DNA Wash Solution, and DNA Elution Solution. These reagents, used in conjunction with an appropriate solid support, are used to generate undegraded DNA, which is substantially pure and contaminant-free. The reagents that may be used to purify DNA from a variety of biological materials without the use of hazardous substances such as phenol, and chloroform, or hazardous chaotropic substances such as guanidinium salts, urea, etc.

(1) DNA Lysing Solutions: A DNA Lysing Solution enables efficient lysis of the biological sample to release the nucleic acids, and effectively inhibits DNase activity. A DNA Lysing Solution of the present invention has the following components: a lithium salt; a buffer; a surfactant, such as a detergent or detergent/surfactant mixture; and optionally a chelating reagent. A DNA Lysing Solution of the present invention is unique in that it requires no added strong chaotropic substances such as guanidinium salts, urea, etc. Guanidinium salts and urea are strong chaotropic salts that disrupt the structure of water and thus tend to decrease the strength of hydrophobic interactions resulting in a drastic effect on other solute molecules. For example, urea, when dissolved in water, disrupts the secondary, tertiary, and quaternary structures of proteins, and subsequently causes dissociation of proteins from DNA. Guanidinium salts and urea dissolve in water through endothermic reactions. Both guanidinium salts and urea are considered to be strongly chaotropic salts as defined by the Hofmeister series, a widely used system that ranks cations and anions according to relative chaotropic strength (F. Hofmeister, *On the understanding of the effects of salts*, Arch. Exp. Pathol. Pharmakol. (Leipzig) 24 (1888) 247-260).

Unlike strong chaotropic salts, the reaction of lithium salts (such as lithium chloride and lithium bromide) in water is an exothermic reaction and is indicative of the tremendous ion-dipole interaction exhibited by the strong kosmotropic lithium ion and the resulting large solubility. Differences such as these are indicative of the differences between the strong chaotropic substances, such as guanidinium salts, and the alkali-metal salts, especially lithium chloride, of the present invention.

The present invention involves the use of lithium salts, including for example, lithium chloride and lithium bromide. The lithium ion is considered very kosmotropic, due to its high surface charge density and strong hydration characteristics. The lithium ion is unique in that it has a small radius, in comparison to that of sodium, potassium, rubidium and cesium ions also found in the alkali metal group. This causes its surface charge density to be larger than the other ions in this group. The larger surface charge density is responsible for the tremendous interaction of the lithium ion with water molecules. This causes water molecules to organize around the ion and to maintain this structured effect even past the first hydration shell.

Suitable DNA-complexing salts for the present invention include those that contain the alkali metal ions such as lithium, sodium, potassium, rubidium and cesium, since all of these cations complex specifically to the phosphate groups of the DNA molecules. This complexation and subsequent neutralization of the DNA molecule cause the DNA molecules to become less stable in the aqueous environment and promotes binding to the solid phase. One embodiment of the present invention is to use a lithium salt. Lithium salts used to practice the present invention include, but are not limited to, lithium chloride and lithium bromide. Lithium fluoride and lithium iodide are less desirable alkali salts because their cost is about five times the cost of the lithium chloride and bromide salts. In addition, lithium ion is the only clearly kosmotropic ion in the aforementioned list. The sodium ion is a borderline kosmotrope, while potassium, rubidium and cesium ions are chaotropic ions (Collins, K. Sticky Ions in Biological Systems, Proc. Natl. Acad. Sci. USA, 92 (1995), 5553-5557). Cesium chloride costs about five times more than the other alkali metal chloride salts (Table 1) and has more limited solubility behavior than the lithium chloride and bromide salts. In addition, sodium, potassium and ammonium chloride salts have much more limited solubility behavior as compared to the lithium chloride and bromide salts, as exhibited by the large exothermic heats of solution exhibited by lithium salts in water (CRC Handbook of Chemistry and Physics, 62nd edition, CRC Press, Boca Raton, Fla.).

Binding of DNA to a solid support is enhanced by high concentrations of alkali metal salts in the Lysing and/or Spiking Solutions. The alkali-metal salt may be at a concentration of between 2-10 M. In Example 2, it is observed that in the Lysing Solution, ammonium and potassium chloride salts have maximum solubility of 3 M and <3 M respectively, while cesium and sodium chloride salts readily dissolve to 4 M. As can be seen in Table 2, these salt values approximately match those expected in aqueous solution, except for that of ammonium chloride (*CRC Handbook of Chemistry and Physics*, 62nd edition, CRC Press, Boca Raton, Fla.).

Alkaline earth metal salts containing the kosmotropic magnesium and calcium ions, although also having properties of forming salt complexes with DNA, however they are not soluble at the high concentrations needed to bind DNA to the solid support. In addition, for example, the alkaline earth metal beryllium is about 20 times more expensive than for the alkaline metal salts lithium chloride or lithium bromide, and therefore is not as practical for use in the present invention.

The DNA Lysing Solution of the present invention contains a lithium salt so that DNA binds to a distinct solid phase through an adsorption mechanism. The use of lithium salt to cause adsorption of DNA to a solid phase differs from the use of lithium for the precipitation of DNA. In the adsorption process, the solvent molecules are separated from the DNA molecules. The interaction between the DNA and the solid phase is energetically more favorable than that of DNA molecular interactions, so that adsorption to the solid phase occurs instead of precipitation. An example of an appropriate solid phase is borosilicate.

The DNA Lysing Solution of the present invention achieves binding of DNA, as compared to other materials in the biological material, to a solid support by the presence of the DNA-complexing lithium salt, such as lithium chloride or lithium bromide, in a buffer, and a surfactant, without the use of hazardous chaotropic substances such as guanidinium salts, urea, etc. The lithium ion binds to the charged phosphate backbone of nucleic acids such as DNA, causing the DNA to be less soluble at high lithium ion concentrations (Kazakov S. A., *Nucleic Acid Binding and Catalysis by Metal Ions*, in Bioorganic Chemistry Nucleic Acids, Ed. Hecht, S. M., Oxford University Press, NY & Oxford, 1996). Thus, the DNA-complexing salt confers unique binding properties to nucleic acids, such as DNA, so that the nucleic acids can bind to the solid support over other contaminants such as proteins, phospholipids, etc.

The second component of the DNA Lysing Solution is a buffer that maintains the pH of the solution. The present invention also teaches the use of a unique neutral to high pH DNA Lysing Solution for maximum DNA yield from various sample types. For example, the DNA Lysing Solution may be buffered to maintain the pH at least about 7, at least about 8, at least about 8.5, or even at least about 9. The buffer may have a pKa of at least about 8, and may be used at a concentration of 10-100 mM. An example of an appropriate buffer is tris (hydroxymethyl)aminomethane (Tris). Optionally, a base may be used to adjust the pH of the DNA Lysing Solution. The base may be one that can raise the pH of the solutions to no less than 7. The base may be an alkali-metal hydroxide. Such alkali-metal hydroxides include sodium hydroxide, potassium hydroxide, and lithium hydroxide.

The DNA Lysing Solution additionally comprises one or more surfactants. A surfactant comprises a molecule that reduces the surface tension of a liquid and by reducing attractions between molecules of similar polarity and structure to allow for solubilization between molecules of differing polarity and structure. In one embodiment, the surfactant is a detergent, or a detergent/surfactant mixture, that aids in lysing the biological material. The detergent is present in order to solubilize membrane components, such as lipids and proteins, in order to facilitate the lysis of cell membranes and the homogenization process. The surfactant is present in order to assist in the solubility of the solution as well as help increase shelf-life of the solution. Anionic, cationic, nonionic and zwitterionic detergents may all be used. In certain instances, DNA isolation is optimally achieved through the use of a non-ionic detergent, while in other instances, DNA isolation is optimally achieved through use of an anionic detergent. Although any nonionic or anionic detergents may be used, examples of non-ionic detergents are those from the Tween class (Tween-20, Tween-40, Tween-60, Tween-80, etc.), the Triton class (X-100, X-114, XL-80N, etc), Tergitols (XD, TMN-6, etc.) and Nonidets or Igepal (NP-40, etc.), and examples of anionic detergents are SDS (sodium dodecyl sulfate) or N-lauroyl sarcosine. The nonionic detergent may be used at a concentration of 5-15%, such as at about 10%. The anionic detergent may be used at a concentration of 0.05-0.2%. In another embodiment, a combination of detergents and surfactants may be used. In one embodiment the surfactant is DGME (diethyl glycol monoethyl ether). In one embodiment, a combination of the detergent Triton-X and surfactant DGME is used. The combination may be at a concentration of 5-15%, such as at about 10%. In one example, the combination is 5% Triton-X and 5% DGME. In yet another embodiment, the combination may be at a concentration of 25-35%, such as about 30%. In one example, the combination is 0.1% SDS and 30% DGME.

The combination of the lithium salt and a detergent or surfactant in a neutral to high pH buffer, also serve to denature enzymes such as DNases, which are generally associated with biological material. Optionally, the DNA Lysing Solution may also contain a chelating agent to complex extraneous metal ions. The chelating agent may be present at a concentration of 1-100 mM, or at a concentration of 1-10 mM. Examples of chelating agents are EDTA or citrate. The DNA Lysing Solution of the present invention possesses significant advantages over other described reagents. The unique combination of the DNA-complexing lithium salt and detergent in a neutral- to high-pH buffer inactivates enzymes harmful to DNA (such as DNases) without the use of such reagents as phenol, chloroform, and guanidinium salts, while allowing for complete lysing of biological material and facilitation of the binding process when used in combination with the DNA Spiking Solutions.

(2) DNA Spiking Solutions: The present invention also teaches of the use of DNA Spiking Solutions that can be used to dehydrate the DNA molecules such as to cause quantitative binding of DNA to the solid phase. The DNA Spiking Solution can be an alcohol. Examples of alcohols are isopropanol, ethanol, or methanol. In one embodiment, the DNA Spiking Solution is 100% alcohol, such as 100% isopropanol. The DNA Spiking Solution can alternatively comprise an alkali-metal salt. The alkali-metal salt DNA Spiking Solution may be buffered or not, such as at pH greater than 7. The alkali-metal salt DNA Spiking Solution may additionally contain optional detergent or surfactant. In one embodiment, the surfactant is DGME.

The DNA Spiking Solution dehydrates the DNA molecules such as to cause quantitative binding of DNA to the solid phase. It has been observed that LiCl will precipitate DNA out of solution at extremely high concentrations (13 molal), where other salts are not sufficiently soluble (Emanuel, C. F. *Some Physical Properties of Deoxyribonucleic Acids Dissolved in a High-Salt Medium: Salt Hyperchromicity, Biochim. Biophys. Acta,* 42, 91-98 (1960)). Higher concentrations of salt or alcohol result in higher yields of DNA bound to glass fiber. At increasingly higher concentrations of LiCl, water molecules are pulled away from nucleic acid hydration shells, to instead bind preferentially to Li$^+$ in solution. One study indicates that at high enough concentrations of LiCl, eventually no water molecules are left bound to the DNA structure (Chattoraj, D. K. & Birdi, K. S. *Adsorption of Water Vapor by Biopolymers, in Adsorption and the Gibbs Surface Excess,* Plenum Press, NY & London, 1984). The dehydration effect and subsequent neutralization of the surface causes the DNA molecules to be forced out of the highly ordered water solution, due to their increased hydrophobicity, and to bind to the solid phase. DNA adsorption to the silica solid phase is also partly driven energetically by the increase in entropy that occurs when water molecules are released from both the DNA molecules and the silica solid phase surface during the dehydration process (Melzak, K. A. et al. *Driving Forces for DNA Adsorption to Silica in Perchlorate Solutions, J. Colloid Interface Science,* 181, 635-644 (1996)). The use of a DNA Spiking Solution consisting of either a high salt concentration or high alcohol composition will more completely dehydrate or salt out the DNA molecules from the solution causing adsorption to the solid phase.

In one embodiment, the DNA Spiking Solution contains a high concentration of an alkali metal salt, such as a lithium salt. In one embodiment, the alkali metal salt is at a concentration of 10-15 M. The DNA Spiking Solution may be buffered to a pH of at least 7. The DNA Spiking Solution may contain a surfactant to assist in the solubility of the salt and buffer. The surfactant may be DGME.

(3) DNA Wash Solution: The present invention also teaches a DNA Wash Solution to wash the solid support to which nucleic acids are bound so as to rid it of non-nucleic acid contaminants or impurities such as proteins and phospholipids, while allowing the nucleic acids to remain bound to the solid support. The Wash Solution contains an alcohol, and a buffer, salt or chelator (EDTA). The buffer composition may be Tris HCl, such as at pH 6-8. The buffer concentration may be at 50-150 mM (e.g., at 100 mM). The alcohol may be ethanol. The alcohol concentration may be at 25-100%. The EDTA concentration may be at 1-20 mM (e.g., at 5-10 mM).

(4) DNA Elution Solution: DNA bound to the solid support may be eluted using a DNA Elution Solution. The simplicity of the reagents used in lysing the biological material and binding of the DNA to the solid support, and in washing the solid support taught by the present invention lends itself to a simple DNA Elution Solution. Other DNA Elution Solutions known to those skilled in the art may also be used. For example, a DNA Elution Solution that may be used is Versagene™ DNA Elution Solution (Gentra Systems, Inc., Minneapolis, Minn.). Alternatively, Tris-EDTA (TE) may be used.

Solid Supports

A variety of solid supports may be used in the present invention. Suitable solid supports include silica-based supports such as glass fiber, or other materials such as cellulose, cellulose acetate, nitrocellulose, nylon, polyester, polyethersulfone, polyolefin, polyvinylidene fluoride, and combinations thereof. The solid support may be encased or immobilized in a vessel to enable plug-flow or continuous-flow DNA isolation methods. Alternatively, the material of the solid support may be packed so as to create a free-standing solid support such as a membrane, disk, or cylinder that may be immobilized or encased in a suitable vessel, such as a tube or plate. In one embodiment, the solid support may be fibrous or particulate to allow optimal contact with the biological material. The size of the solid support suitable for use with the reagents of this invention may vary according to the volume of biological material. For example, glass fiber membranes may be cut to different sizes, in order to allow for the binding, purification and elution of different quantities of DNA.

In one embodiment, the solid support may be a material that permits the binding of nucleic acids to the solid support instead of other biological contaminants in the presence of the aforementioned DNA Lysing Solution described above. Such a solid support may be a silica-based or borosilicate glass fiber material. Glass fiber materials provide a better yield because of the specific binding properties to the electropositive silicon and boron atoms, and because of hydrogen bonding properties of the silicate surface. Because of the specificity of silica for nucleic acids, more DNA is bound relative to other contaminants and the eluted product is made more substantially pure.

The shape of the solid support suitable for use with the reagents of this invention may be, for example, a sheet, a precut disk, cylinder, single fiber, or a solid support composed of particulates. The material of the solid support may be packed so as to create a free-standing solid support such as a membrane, disk, or cylinder that may be immobilized or encased in a suitable vessel. If necessary, the solid support is contained in an appropriate vessel, e.g., a paper form (such as a Guthrie card), a microcentrifuge tube, a spin tube, a 96-well plate, a chamber, or a cartridge. If the solid support comprises fibers, it may be encased in a suitable vessel so as to pack the fibers appropriately, allow for optimal nucleic acid binding, and the washing away of contaminants such as protein, phospholipids, etc.

The solid support may be pre-treated with RNase solution in order to degrade RNA present in the biological sample. Additionally, using the pre-treated columns eliminates the need for a separate RNase digestion step, as is typically required in conventional methods.

Optionally, purification may be improved by the use of RNase-treated columns (Gentra Systems, Inc.). The RNase-treated columns degrade RNA present in the biological sample. Additionally, using the pre-treated columns eliminates the need for a separate RNase digestion step, as is typically required in conventional methods. In another embodiment of the invention, the DNA Lysing Solution may be added directly to the material (e.g., fibers, etc.) used in making the solid support and may be allowed to dry before it is made into the final user-ready form (e.g., paper, swab, disk, plug, column, etc.). The use of RNase-treated columns (Gentra Systems, Inc.) reduces the number of steps in the purification process as well as time to process DNA samples.

In order that the invention may be better understood, specific embodiments for vessels that contain the solid support will now be described in more detail. In one embodiment of this invention, the vessel is a cartridge equipped with one or more inlet ports or pierceable septa at the top. The inlet ports are attached to vessels upstream containing the sample or reagents through a connector, such as a female Luer-Lock. One inlet, the sample port, is used for the application of the biological sample to the solid support. An optional feature on the sample port is a self-sealing mechanism that seals the sample port after sample has been transferred through it. The second inlet serves as a reagent port. An optional feature on both inlet ports is a protective breakaway seal. Furthermore, the inlet ports, breakaway seals and diffuser may be housed in an optional screw-cap. The versatility and effectiveness of the DNA Lysing Solution lends itself to two viable alternative methods for DNA isolation. In the first method, the biological material is contacted with the DNA Lysing Solution before it is contacted with the solid support. In one embodiment, when the biological material comprises cellular or viral material, the DNA Lysing Solution is used to lyse the cells and release the nucleic acids, including DNA. In the second method, the DNA Lysing Solution is added directly to the solid support and allowed to bind to the solid support, thereby eliminating a step, and further simplifying the method. In this latter method, the DNA Lysing Solution is directly applied to the solid support and then dried on the solid support before contacting the biological material with the treated solid support.

At the bottom of the solid support is an optional diffuser with a pore size suitable for the dispersion and passage of cellular debris, proteins and lipid molecules. The diffusers allow for a uniform traversal of biological material across the cross section of the cartridge, and prevent unequal buildup of biological material anywhere above or below the solid support. The outlet of the cartridge comes equipped with a protective cap that fits neatly over the tapered barrel. The purified DNA is collected in a collection tube that consists of a conical tube with a snap cap for easy and contamination-free storage. The entire vessel can be scaled in size depending on the size of the samples to be processed and the yields needed for subsequent analysis.

In another embodiment of this invention, the vessel is a spin tube designed to hold an insert into which the solid support is packed. The solid support may be silica-based, cellulose, cellulose acetate, nitrocellulose, nylon, polyester, polyethersulfone, polyolefin, polyvinylidene fluoride, and combinations thereof. In one embodiment, the support is a silica-based borosilicate glass fiber membrane. The insert has a flanged top to hold it in the spin tube and a perforated bottom to allow fluids to pass through while supporting the solid support. A cap tethered to the spin tube may be used to cover the insert. Solutions, for instance, DNA Lysing Solution containing non-nucleic acid contaminants, DNA Wash Solutions, or DNA Elution Solution containing DNA, pass through the perforated bottom and are collected at the bottom of the spin tube by centrifugal forces that draw out the solutions.

In yet another embodiment, the vessel may be multiple well plates, for example, 6, 12, 24, 48, 96, or 384 well plates where a solid support is packed into each well. The bottom of each well has an exit port through which solutions containing contaminants or purified DNA can pass.

The unique combination of the solid support of choice with the unique reagents—DNA Lysing Solutions, DNA Spiking Solutions, DNA Wash Solution, and DNA Elution Solution—results in the isolation of substantially pure, undegraded DNA. The properties of the DNA Lysing and Spiking Solutions as described above permit superior lysing and binding of the nucleic acids to the solid support, while the DNA Elution Solution and optional RNase-treated column permits the preferential elution of the DNA from the solid support.

Kits

The present invention also provides kits for purifying DNA that contain instruction means for preparing substantially pure and undegraded DNA from a biological sample and one or all of the following: DNA Lysing Solution, either as a separate solution or pretreated onto a solid support, a solid support either untreated or treated with a DNA Lysing Solution, a DNA Spiking Solution, a DNA Wash Solution, a DNA Elution Solution or any combination thereof. In addition, the kit can include auxiliary components such as a proteinase K solution, a vessel to contain the solid support, vessels to contain substantially pure and undegraded DNA, and combinations thereof. Substantially pure, undegraded DNA is DNA that is suitable for use in subsequent analyses known to those with skill in the art, for example, nucleic acid quantification, restriction enzyme digestion, DNA sequencing, hybridization technologies, such as Southern Blotting, etc., and amplification methods such as Polymerase Chain Reaction (PCR), Ligase Chain Reaction (LCR), Nucleic Acid Sequence Based Amplification (NASBA), Self-sustained Sequence Replication (SSR or 3SR), Strand Displacement Amplification (SDA), and Transcription Mediated Amplification (TMA), Quantitative PCR (qPCR), or other DNA analyses.

The reagents, methods and kits of the present invention provide substantially pure and undegraded DNA with relatively little contaminating RNA or other impurities such that the DNA may be used in downstream processes such as nucleic acid quantification, restriction enzyme digestion, DNA sequencing, hybridization technologies, such as Southern Blotting, etc., and amplification methods such as Polymerase Chain Reaction (PCR), Ligase Chain Reaction (LCR), Nucleic Acid Sequence Based Amplification (NASBA), Self-sustained Sequence Replication (SSR or 3SR), Strand Displacement Amplification (SDA), and Transcription Mediated Amplification (TMA), Quantitative PCR (qPCR), or other DNA analyses.

Methods

The present invention also provides methods for purifying DNA from biological material. The reagents and solid supports taught in the invention lend themselves to alternate isolation methods.

In one embodiment of a method of the present invention, the biological material is contacted with the DNA Lysing Solution before it is contacted with the solid support. The DNA Lysing Solution is used to lyse the biological material and release the DNA before adding it to the solid support. Additionally, the DNA Lysing Solution prevents the deleterious effects of harmful enzymes such as DNAses. The DNA Lysing Solution may be successfully used to lyse cultured cells or white blood cells in pellets, or to lyse cells adhering to or collected in culture plates, such as standard 96-well plates. If the biological material is composed of tissue chunks or small particles, the DNA Lysing Solution may be effectively used to grind such tissue chunks into a slurry because of its effective lysing capabilities. The DNA Lysing Solution volume may be scaled up or down depending on the cell numbers or tissue size. Once the biological material is lysed, a DNA Spiking Solution is added to the lysate and then added to the solid support.

In another embodiment, the DNA Lysing Solution may be added directly to the solid support, thereby eliminating a step, and further simplifying the method. In this latter method, the DNA Lysing Solution may be applied to the solid support and then dried on the solid support before contacting the biological material with the treated solid support.

RNase may be added either directly to the solid support to pre-treat the column or added to the Lysing Solution to degrade RNA present in the biological sample. Using the pre-treated columns and/or RNase added to the Lysing Solution, eliminates the need for a separate lysis and/or RNase digestion steps, as is typically required in conventional methods.

When the biological materials comprise cellular or viral materials, direct contact with the DNA Lysing Solution, or contact with the solid support pre-treated with the DNA Lysing Solution and/or an RNase solution, causes the cell and nuclear membranes, or viral coats, to solubilize and/or rupture, thereby releasing the nucleic acids as well as other contaminating substances such as proteins, phospholipids, etc.

In a third embodiment, the reagents of the present invention could be used in a direct-lysis method, which may be useful for example, with whole blood. This method eliminates the need to perform a red blood cell lysis step common in most other whole blood purification methods. In this method, a first DNA Lysing Solution is added to the biological material. The first DNA Lysing Solution comprising an alkali metal salt and a non-ionic detergent. A second DNA Lysing Solution comprising an alkali metal salt and an anionic detergent is added to the biological material. The use of two lysis solutions is helpful in order to successfully lyse and solubilize all blood cells during the direct lysis of large volumes of blood.

In a fourth embodiment of the method of the present invention, DNA can be effectively purified from, for example, fixed cells or cervical swab media or fixed cervical cells. The Lysing Solution comprising an anionic detergent is simply added to the biological material, pipetted up and down to lyse the cells and denature proteins. Following the lysis step, using proteinase K solution may be essential for certain types of sample, for example, cervical swab media. For these samples, proteinase K is added and the sample mixed by vortex. Samples may be incubated for 2-3 hours at 65° C.

After, the lysis steps of any of the above methods, a DNA Spiking Solution may be used to dehydrate the DNA molecules such as to cause quantitative binding of DNA to the solid phase. Next, the biological material is optionally removed by suitable means such as centrifugation, pipetting, pressure, vacuum, or by the combined use of these means with a DNA Wash Solution such that the nucleic acids are left bound to the solid support. The remainder of the non-nucleic acid biological material that includes proteins, phospholipids, etc., may be removed first by centrifugation. By doing this, the unbound contaminants in the lysate are separated from the solid support.

Subsequently, the bound DNA may be eluted using an adequate amount of a DNA Elution Solution known to those skilled in the art. The solid support may then be centrifuged, or subjected to pressure or vacuum, to release the DNA from the solid support and can then be collected in a suitable vessel.

As another aspect of this invention, a kit is provided that includes specific protocols, which in combination with the reagents and optionally the solid supports described herein, may be used for purifying DNA from biological materials according to the methods of the invention.

This invention will be further described by reference to the following detailed examples. These examples are offered to further illustrate the various specific and illustrative embodiments and techniques. It should be understood, however, that many variations and modifications may be made while remaining within the scope of the present invention.

All of the raw materials mentioned below are readily available from commercial sources such as Sigma Chemical Company, St. Louis, Mo. All percentages are in volume per volume, based on the total volume of the reagent, unless specified otherwise.

EXAMPLES

Example 1

Cost Analysis

In order to produce the best quality solid phase DNA purification product, the product must function exceptionally well in several respects. The solid phase DNA purification product must effectively isolate a pure DNA sample from a variety of sample types and result in the highest possible yields of DNA. It must be user friendly, meaning the steps must not be too onerous, and the components must not be toxic and can be disposed of easily. Further, the product must be economical for the user. Therefore, finding cost effective components for the solutions was essential. Table 1 shows the cost for each of the salts evaluated herein.

TABLE 1

| Salt | Cost | |
|------|------|------|
|      | Amount (grams) | Cost ($) |
| $BeCl_2$ | 25 | 600.00 |
| $CaCl_2$ | 500 | 105.00 |
| CsCl | 500 | 340.00 |
| KCl | 500 | 30.00 |
| LiBr | 500 | 65.00 |
| LiCl | 500 | 60.00 |
| LiF | 50 | 400.00 |
| LiI | 250 | 330.00 |
| $MgCl_2$ | 500 | 50.00 |
| NaCl | 500 | 24.00 |
| $NH_4Cl$ | 500 | 22.00 |

Although the lithium salts work well for the methods of the present invention, the lithium salts LiF and LiI are expensive, and additionally, LiF is quite hazardous. LiCl and LiBr both work well with the methods of the present invention and cost about the same at $60-65 per 500 grams. KCl, NaCl, and $NH_4Cl$ are all economical, but do not result in the DNA yields desired.

Example 2

Solubility and Heat of Solution Data for Chloride Salts and Compared to LiCl and LiBr Salts for Solid Phase DNA Purification Procedure The solubility and performance of several chloride salts was examined and compared to two lithium salts, lithium chloride and lithium bromide. The DNA Lysing Solution was prepared using other chloride salts, in order to examine maximum solubility obtainable in both the buffer and detergent based DNA Lysing Solution. Table 2 shows the approximate maximum solubility as measured in this work and compares it to tabulated solubility data extrapolated to 20° C., as well as tabulated heat of solution data as obtained from the Handbook of Chemistry and Physics (62nd edition, CRC Press, Boca Raton, Fla.).

The solubility of most of the chloride salts studied in the Lysing Solution, were comparable to the lithium chloride and bromide salts at a concentration of 4 M, except for those of potassium chloride and ammonium chloride. The expected solubility of potassium chloride was low, when compared to the solubility of the other salts, at only approximately 3 M in aqueous solution. The other salts were expected to be more soluble than 4 M in aqueous solution, however it was observed that the ammonium chloride salt is only soluble to approximately 3 M, when compared to the expected solubility of about 7 M. This could be due to the presence of surfactant, for example Triton X-100 (5%) and DGME (5%) in solution, since the combination for these components in solution was 10%. Except for the salts, the remainder of the DNA Lysing Solution was kept constant within all solutions and contained, 5% Triton X-100, 5% DGME (diethylene glycol monoethyl ether), 10 mM EDTA, 10 mM TCEP, 1% sodium tungstate, in 100 mM TRIZMA at pH 8.8.

The large exothermic heats of solution for lithium chloride and lithium bromide in water provided substantiation as to the large solubilities demonstrated by lithium salts in general. The other chloride salts in this example exhibited endothermic heats of solution, indicating that solvation of these salts was not as favorable in aqueous solution as for the lithium salts.

Tergitol, Nonidet and Igepal family of detergents were examined along with a number of surfactant compounds.

It was discovered that many of these detergent formulations, when mixed with the other ingredients of the DNA Lysing Solution, saponified or degraded over time and precipitated out of solution. For example, this occurred with 10% Tween-20 (polyoxylene sorbitan monolaurate). Similar performance was found using an equal mixture of Triton X-100 (t-octylphenoxy polyethoxyethanol) and Tween-20, though this mixture was stable for longer periods of time. This mixture, however, eventually saponified and separated. DGME (diethylene glycol monoethyl ether) was chosen for testing as a surfactant to help solubilize the salt and detergent combinations. A mixture of Triton-X at 5% and DGME at 5% was found to work particularly well to maintain solubility of the first DNA Lysing Solution.

DNA extraction from cervical cells proved to be particularly challenging, as Proteinase K digestion is required for robust collection of DNA from this sample type. The presence of sodium dodecyl sulfate (SDS) worked best in the Lysing Solution in order to obtain the highest Proteinase K activity. The optimal concentration was determined by systemically testing a variety of DNA Lysing Solution with Proteinase K treatment. Higher concentrations of SDS (greater than 0.1% SDS final concentration) precipitate out of the Lysing Solution at temperatures above or below room temperature, causing the Proteinase K activity to be lower than required. Lower concentrations of SDS (less than 0.1% final concentration) disallow full Proteinase K activity, which is helpful for complete lysis of fixed cell preparations like cervical cells. DGME was also included in this second DNA Lysing Solution to allow for the SDS and LiCl salt to remain soluble through the lysing, spiking and binding processes.

The major technical hurdle for the development of the direct lysis process for whole blood was the lysis efficiency of detergents in whole blood. The initial testing focused on the use of the non-ionic detergent Triton X-100 for cell lysing. The use of this detergent resulted in low DNA recovery in the direct lysis method, probably due to the interference of red blood cells and red blood cell lysate being present in the solution. Triton X-100 is not a protein denaturant and due to the high levels of cellular contamination it was decided to try

TABLE 2

| Salt | Measured Solubility in Lysing Solution | Reported Solubility in Water* | Reported Solubility in Alcohol(s) | Heat of Aqueous Solution (kcal/mole) | Type of Heat |
|---|---|---|---|---|---|
| LiCl | at least 4M | 18M | soluble in alcohol | −8.85 | exothermic |
| LiBr | at least 4M | 19M | soluble in alcohol & ethanol | −11.67 | exothermic |
| CsCl | at least 4M | 11M | very soluble in alcohol | +4.25 | endothermic |
| NH4Cl | 3M | 7M | insoluble ethanol | +3.53 | endothermic |
| NaCl | at least 4M | 6M | slightly sol in alcohol | +0.93 | endothermic |
| KCl | less than 3M | 3M | slightly sol in alcohol, soluble in ethanol | +4.12 | endothermic |

*Note:
Data extrapolated to 20° C. from tabulated data in Handbook of Chemistry and Physics.

Example 3

Evaluation of Detergents for DNA Purification

Much time and effort was spent screening detergents that would adequately lyse cells and also stay soluble in the DNA Lysing Solution of the present invention. The Tween, Triton, a detergent that was a proven protein denaturant. To increase the lysis efficiency, the anionic detergent sodium dodecyl sulfate (SDS) was tested in place of the non-ionic detergent. This increased DNA recovery but resulted in clogging of the purification membrane. Previous work with cell pellets had shown that a combination of both detergents resulted in increased DNA recovery. The use of both detergents in the direct lysis method resulted in an increase in DNA recovery and the elimination of membrane clogging. Testing the order of detergent addition (anionic/non-ionic vs. non-ionic/anionic) showed that for optimal DNA recovery, the non-ionic detergent had to be added before the anionic detergent.

Example 4

Isolation of DNA from Blood by Direct Lysis Method

An equal volume of the first DNA Lysing Solution (6 M LiCl, 5% Triton X-100, 5% DGME (diethylene glycol monoethyl ether), 10 mM EDTA, in 100 mM Tris at pH 8.8) was added to the whole blood samples. The resulting solution was pipetted up and down five times, pulse vortexed five times at high speed, pipetted up and down 20 times, and then pulse vortexed again five times, in order to achieve complete homogenization. After homogenization, two blood volumes of the second DNA Lysing Solution (25 mM Citrate, 2 M LiCl, 0.1% SDS, 30% DGME, in 25 mM Tris at pH 9.1) were added to the samples. The samples were mixed following the same process as described for the First DNA Lysing Solution. After homogenization and lysis with the two lysis solutions, four blood volumes of DNA Spiking Solution (10 M LiCl, 10% DGME, 100 mM Tris at pH 7.9) were added to each sample. The resulting solution was pipetted up and down five times to mix.

After homogenization, 600 µL of each homogenized lysate was pipetted onto each purification column. The purification column contained a borosilicate glass fiber membrane (Whatman D glass fiber membrane) within a basket and placed inside a vacuum elution station. The lysates were pulled through the membrane using vacuum filtration. The remaining lysates were added, 600 µL at a time, to the column and removed using vacuum filtration.

After vacuum filtration of each lysate and subsequent binding of DNA to the borosilicate membrane surface, 400 µL of DNA Wash Solution (5 mM EDTA, 70% ethanol, in 100 mM Tris HCl at pH 7.6) was added to the column material and removed with vacuum for 30 seconds. The DNA Wash Solution addition and vacuum filtration steps were repeated once into the same elution tube.

To elute the DNA from the solid support, the basket containing the membrane was transferred to a microfuge tube and 50 µL of DNA Elution Solution (1 mM EDTA in 10 mM Tris at pH 7.5) solution was added to the column material, incubated for five minutes and spun at maximum speed for one minute. The addition of DNA Elution Solution, the five minute incubation and centrifugation steps were repeated once. Purifications from five blood volumes were performed (300 mL, 500 mL, 1 mL, 1.5 mL and 3 mL), and were electrophoresed and compared to 200 ng of Lambda Hind III ladder. The results indicated that intact, high molecular weight DNA could be purified from whole blood using the direct lysis method from a large range of whole blood input volumes.

Example 5

Isolation of DNA from Blood Using RBC Lysis Method

One embodiment of the invention used for the isolation of DNA from a whole blood sample was to first lyse the red blood cells in the blood sample, followed by pelleting of the white blood cells from the resulting red blood cell lysate using centrifugation. After the red blood cell lysate supernatant was poured off and the white blood cell pellet was washed and repelleted, 200 µL of DNA Lysing Solution (6 M LiCl, 5% Triton X-100, 5% DGME (diethylene glycol monoethyl ether), 10 mM EDTA in 100 mM Tris at pH 8.8) was added to the pellet, to lyse the white blood cells by vortexing and pipetting in the DNA Lysing Solution to thoroughly homogenize the sample. After homogenization, 400 µL of DNA Spiking Solution (10 M LiCl, 10% DGME, 100 Tris at pH 7.9) was added to the white blood cell lysate and the mixture was added to the purification column containing a borosilicate glass fiber membrane (Whatman D glass fiber membrane) within a basket and placed inside a 2 mL microfuge tube. The microfuge tube was then spun at 7000×g for 1 minute. After lysate centrifugation, 400 µL of DNA Wash Solution (5 mM EDTA, 70% ethanol, in 100 mM Tris HCl at pH 7.6) was added to the column material and spun at maximum speed in a microcentrifuge for one minute. The DNA Wash Solution addition and centrifugation steps were repeated once. To elute the DNA from the solid support, the basket containing the membrane was transferred to a new microfuge tube and 50 µL of DNA Elution Solution (1 mM EDTA in 10 mM Tris at pH 7.5) was added to the column and spun at maximum speed in a microcentrifuge for one minute. The DNA Elution Solution addition and centrifugation steps were repeated once into the same elution tube.

Figure 1:
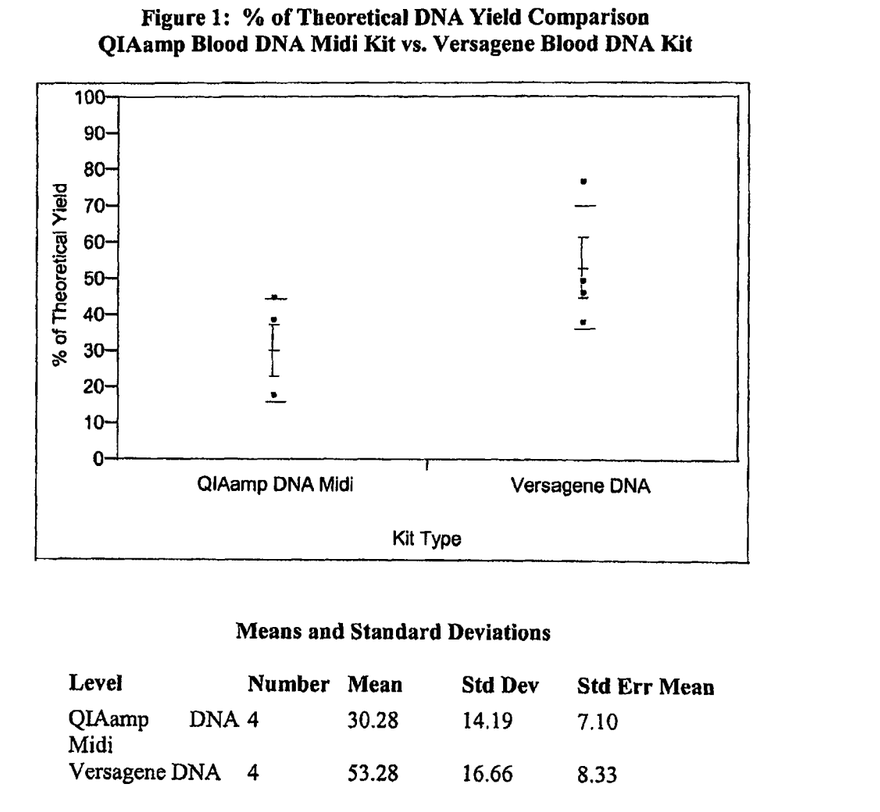
FIG. 1 is a graph depicting the percentage of theoretical DNA yield comparing QIAamp Blood DNA Midi Kit (Qiagen, Inc. Germany) and Versagene Blood DNA Kit (Gentra Systems, Inc., Minnesota).
Figure 2:
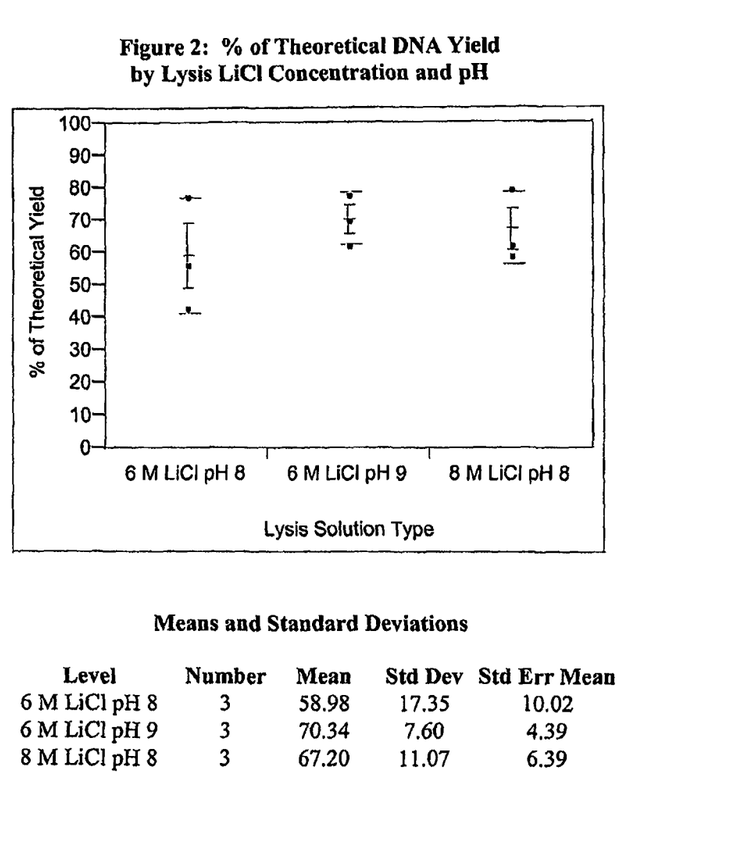
FIG. 2 is a graph depicting the percentage of theoretical DNA yield comparing lithium salts and pH of the lysis solution.

In a direct comparison with the QIAamp Blood DNA Midi Kit (Qiagen Inc., Germany) the Versagene Blood DNA mean yield is approximately double the QIAamp mean yield value for 2 mL blood samples as shown in FIG. 1. The percent of theoretical yield calculation is based on the assumption that six pg of genomic DNA are present per white blood cell. Yields as high as 70-80% of expected theoretical yields were obtained in some cases using the RBC Lysis Method as shown in FIG. 2 using two mL blood samples, where DNA Lysing Solution formulations were varied for pH and LiCl concentration.

Example 6

Isolation of DNA from Cervical Cells

Since it is typically difficult to extract nucleic acid from cervical cell swab media or fixed cervical cells, it can be used effectively to illustrate the efficiency of the compositions and methods of the invention. The skilled artisan will understand, however, that the disclosed compositions and methods may also be effectively employed using a broad range of biological samples and that the invention is not to be limited to use with any sample type.

Cervical cell samples were collected in ThinPrep® Pap Test™ (Cytyc, Boxborough, Mass. and spun down 2,200×g for 5 minutes and then resuspended in PBS to wash cells. The resuspended cells were placed into microfuge tubes and spun down at 14,000×g for 15 seconds. The PBS supernatant was removed from the cervical cell pellet. Each tube was vigorously vortexed to resuspend the cells; this greatly facilitated cell lysis. 200 µL of Lysing Solution (25 mM Citrate, 2 M LiCl, 0.1% SDS, 30% DGME, in 25 mM Tris at pH 9.1) was added to the sample to the resuspended cells and pipetted up and down to lyse the cells and denature proteins. 1.0 µL of Proteinase K Solution (20 mg/ml) was added to the cell lysate and mixed by brief vortex; then incubated the samples at 65° C. for 2-3 hours. 400 µL of 100% Isopropanol DNA Spiking Solution was added to the sample. The samples were pulse vortexed for 30 seconds and then allowed to sit for two minutes prior to loading on to columns. The sample was loaded on to a pre-treated RNase A treated purification column (Gentra Systems, Inc.). The sample was centrifuged at 7,000×g for one minute. The basket containing the purification column was transferred to a new clear tube. 200 μL of DNA Wash Solution (5 mM EDTA, 70% ethanol, in 100 mM Tris HCl at pH 7.6) was added to each purification column. The purification columns were then centrifuged at 7,000×g for one minute. An additional 200 μL of DNA Wash Solution was added to each purification column. The purification columns were then centrifuged at 7,000×g for two minutes. The basket containing the purification column was carefully transferred to a new clear tube. 50 μL of DNA Elution Solution (1 mM EDTA in 10 mM Tris at pH 7.5) was added to each purification column and allowed to incubate at room temperature for five minutes. The purification columns were then centrifuged at 14,000×g for one minute.

In a direct comparison with the Puregene Liquid Chemistry (Gentra Systems, Inc.), the Versagene Solid Phase DNA Chemistry (Gentra Systems, Inc.) mean yield is similar regardless of starting cervical sample type, as shown in the Tables below.

TABLE 3

| Pooled SurePath Pellets | Puregene | Puregene 260/280 Ratio | Versagene | Versagene 260/280 Ratio | % Yield of Versagene Compared to Puregene |
|---|---|---|---|---|---|
| Apr. 30, 2004 | 16.88 | 1.78 | 4.94 | 1.82 | 29% |
| May 3, 2004 | 14.78 | 1.82 | 2.48 | 1.74 | 17% |
| May 6, 2004 | 23.40 | 1.85 | 3.45 | 1.82 | 15% |
| May 20, 2004 | 10.63 | 1.81 | 4.93 | 1.79 | 46% |
| May 24, 2004 | 22.72 | 1.82 | 3.17 | 1.70 | 14% |
| May 27, 2004 | 13.44 | 1.81 | 1.53 | 1.62 | 11% |
| Jun. 2, 2004 | 31.62 | 1.79 | 6.23 | 1.79 | 20% |
| Jun. 4, 2004 | 15.31 | 1.83 | 8.72 | 1.78 | 57% |
| Jun. 8, 2004 | 39.98 | 1.82 | 21.37 | 1.82 | 53% |
| Jun. 9, 2004 | 23.10 | 1.83 | 7.58 | 1.82 | 33% |
| Jun. 15, 2004 | 41.20 | 1.81 | 6.68 | 1.76 | 16% |
| Jun. 16, 2004 | 18.30 | 1.82 | 4.66 | 1.77 | 25% |
| Jun. 17, 2004 | 14.74 | 1.79 | 2.89 | 1.73 | 20% |
| Jun. 18, 2004 | 12.05 | 1.79 | 2.22 | 1.39 | 18% |
| Jun. 29, 2004 | 18.30 | 1.85 | 4.33 | 1.76 | 24% |
| Jun. 30, 2004 | 8.88 | 1.77 | 3.10 | 1.62 | 35% |
| Jul. 2, 2004 | 34.67 | 1.81 | 7.86 | 1.77 | 23% |
| Jul. 8, 2004 | 7.03 | 1.82 | 2.66 | 1.85 | 38% |
| Average | 20.39 | 1.81 | 5.49 | 1.74 | 27% |
| StdDev | 10.30 | 0.02 | 4.49 | 0.11 | NA |

TABLE 4

| Pooled ThinPrep Liquid | Puregene | Puregene 260/280 Ratio | Versagene | Versagene 260/280 Ratio | % Yield of Versagene Compared to Puregene |
|---|---|---|---|---|---|
| Jun. 18, 2004 | 7.71 | 1.80 | 8.30 | 1.73 | 108% |
| Jul. 13, 2004 | 6.45 | 1.82 | 5.64 | 1.77 | 87% |
| Average | 7.08 | 1.81 | 6.97 | 1.75 | 98% |
| StdDev | 0.89 | 0.01 | 1.88 | 0.03 | NA |

TABLE 5

| Pooled SurePath Liquid | Puregene | Puregene 260/280 Ratio | Versagene | Versagene 260/280 Ratio | % Yield of Versagene Compared to Puregene |
|---|---|---|---|---|---|
| Jun. 18, 2004 | 5.75 | 1.60 | 4.07 | 1.47 | 71% |
| Jun. 21, 2004 | 6.00 | 1.82 | 4.72 | 1.81 | 79% |
| Average | 5.88 | 1.71 | 4.40 | 1.64 | 75% |
| StdDev | 0.18 | 0.16 | 0.46 | 0.24 | NA |

NA = Not applicable

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

We claim:

1. A method for isolating substantially pure and undegraded genomic DNA from biological material, comprising the steps of:
    (a) contacting the biological material with a DNA Lysing Solution to form a mixture, wherein
        (i) the DNA Lysing Solution is buffered at pH of greater than 7,
        (ii) the DNA Lysing Solution comprises a lithium salt and at least one surfactant, and
        (iii) the DNA released from the biological material by the DNA Lysing Solution is substantially undegraded;
    (b) contacting the mixture of step (a) with a DNA Spiking Solution;
    (c) contacting the mixture of step (b) to a solid support such that DNA present in the biological material binds to the solid support;
    (d) washing the solid support with a Wash Solution; and
    (e) eluting the DNA with a DNA Elution Solution,
    thereby isolating substantially pure and undegraded genomic DNA from the biological material.

2. The method of claim 1, wherein the DNA spiking solution comprises an alcohol.

3. The method of claim 2, wherein the alcohol may be a mixture of alcohols.

4. The method of claim 2, wherein the alcohol is 100% isopropanol.

5. The method of claim 1, wherein the DNA Spiking Solution contains an alkali-metal salt greater than 1 M.

6. The method of claim 1, wherein the biological material is a cervical cell sample.

7. The method of claim 1, wherein the biological material is whole blood.

8. The method of claim 1, wherein the biological material is a cultured cell, fixed cell, and/or tissue sample.

9. The method of claim 1, wherein the Wash Solution is buffered at a pH of greater than about 7.

10. The method of claim 1, wherein the DNA Lysing Solution lack a chaotrope and/or a strong chaotropic substance.

11. The method of claim 1, wherein the solid support comprises components of silica, cellulose, cellulose acetate, nitrocellulose, nylon, polyester, polyethersulfone, polyolefin, or polyvinylidene fluoride, or combinations thereof.

12. The method of claim 1, wherein the solid support is a solid support which has been pre-treated with RNase solution prior to contacting the biological material with the solid support.

13. The method of claim 1, wherein the lithium salt of the Lysing Solution is lithium chloride or lithium bromide.

14. The method of claim 1, wherein the lithium salt of the Lysing Solution is present at a concentration greater than about 1 M.

15. The method of claim 1, wherein the lithium salt of the Lysing Solution is present at a concentration of between 2 M and 8 M.

16. The method of claim 1, wherein the DNA Lysing Solution further comprises a chelating agent.

17. The method of claim 16, wherein the chelating agent is EDTA or citrate.

18. The method of claim 1, wherein the DNA Lysing Solution comprises a surfactant at a concentration of between about 25-35% v/v.

19. The method of claim 1, wherein the surfactant is a detergent.

20. The method of claim 19, wherein the detergent is a non-ionic detergent.

21. The method of claim 20, wherein the non-ionic detergent is a Tween, Triton, Nonidet, Igepal or Tergitol.

22. The method of claim 19, wherein the detergent is an anionic detergent.

23. The method of claim 22, wherein the anionic detergent is SDS (sodium dodecyl sulfate) or N-lauroyl sarcosine.

24. The method of claim 1, wherein the surfactant is a mixture of detergents, or a mixture of detergents with a solubilizing surfactant.

25. The method of claim 24, wherein the solubilizing surfactant is diethylene glycol monoethylether (DGME).

26. A method for purifying substantially pure and undegraded genomic DNA from biological material, comprising the steps of:
    (a) contacting a biological material containing DNA with a solid support pre-treated with a DNA Lysing Solution, wherein
        (i) the DNA Lysing Solution is buffered at a pH of greater than about 7 and comprises a surfactant and a lithium salt,
        (ii) the biological material is lysed to release nucleic acids comprising substantially undegraded DNA and non-nucleic acid biological matter, and
        (iii) the nucleic acids comprising substantially undegraded DNA bind to the solid support;
    (b) adding a DNA Spiking Solution to the biological material mixture of step
    (c) washing the solid support with a Wash Solution to remove biological materials other than bound nucleic acids comprising undegraded DNA; and
    (d) eluting the bound undegraded genomic DNA from the solid support with a DNA Elution Solution.

27. A direct lysis method for purifying substantially pure and undegraded genomic DNA from biological material without using a red blood cell lysis step, comprising:
    (a) contacting a biological material containing DNA, with a first DNA Lysing Solution, wherein the first DNA Lysing Solution is buffered at a pH of greater than about 7 and comprises a surfactant at a concentration of between about 5-15% v/v and a DNA-complexing salt at a concentration of greater than 1 M,
    (b) contracting the biological material with a second DNA Lysing Solution, wherein the second DNA Lysing Solution comprises a surfactant and a DNA-complexing salt greater than 1 M;
    (c) contacting the mixture of step (b) with a DNA Spiking Solution;
    (d) contacting the mixture of step (c) with a solid support, wherein nucleic acids comprising substantially undegraded DNA from the biological material bind to the solid support;
    (e) washing the solid support with a DNA Wash Solution to remove biological materials other than bound nucleic acids comprising substantially undegraded DNA, the DNA Wash Solution comprising a DNA-complexing salt and an alcohol; and (f) preferentially eluting the bound substantially undegraded genomic DNA from the solid support with a DNA Elution Solution.

28. The method of claim 27, wherein the second DNA Lysing Solution further comprises a chelating agent.

29. A method for purifying substantially pure and undegraded genomic DNA from biological material comprising:
   (a) contacting a biological material containing DNA with DNA Lysing Solution buffered at a pH of greater than about 7, wherein the DNA Lysing Solution comprises a surfactant and a DNA-complexing salt at a concentration greater than 1 M;
   (b) contacting the biological material mixture of step (a) to a solid support, wherein nucleic acids comprising substantially undegraded DNA bind to the solid support;
   (c) contacting the solid support with a DNA Spiking Solution;
   (d) washing the solid support with a DNA Wash Solution to remove biological materials other than bound nucleic acids comprising undegraded DNA, the DNA Wash Solution comprising a DNA-complexing salt and an alcohol; and
   (e) preferentially eluting bound substantially undegraded genomic DNA from the solid support with a DNA Elution Solution.

30. A method for purifying substantially pure and undegraded genomic DNA from a fixed cervical cell sample, comprising the steps of
   (a) contacting a biological material containing DNA with DNA Lysing Solution buffered at a pH of greater than about 7, wherein the DNA Lysing Solution comprises a surfactant at a concentration of between about 25-35% v/v, a chelating agent, and a DNA-complexing salt of greater than 1 M, wherein the biological material is a fixed cervical cell sample;
   (b) adding to the mixture of step (a), an optional DNA Spiking Solution containing alcohol;
   (c) contacting the biological material mixture of step (a) or step (b) to the solid support in order to release nucleic acids comprising substantially undegraded DNA and non-nucleic acid biological matter causing nucleic acids comprising substantially undegraded DNA to bind to the solid support;
   (d) washing the solid support with a DNA Wash Solution to remove biological materials other than bound nucleic acids comprising undegraded DNA; and
   (e) preferentially eluting the bound undegraded DNA from the solid support with a DNA Elution Solution in order to obtain substantially pure and undegraded genomic DNA.

31. The method of claim 2, wherein the alcohol is isopropanol, ethanol or methanol.

32. The method of claim 1, wherein the Wash Solution lack a chaotrope and/or a strong chaotropic substance.

33. The method of claim 1, wherein the DNA Lysing Solution and the Wash Solution lack a chotrope and/or a strong chaotropic substance.

34. The method of claim 1, wherein the genomic DNA is or comprises viral genomic DNA.

35. The method of claim 26, wherein the genomic DNA is or comprises viral genomic DNA.

36. The method of claim 27, wherein the genomic DNA is or comprises viral genomic DNA.

37. The method of claim 29, wherein the genomic DNA is or comprises viral genomic DNA.

38. The method of claim 30, wherein the genomic DNA is or comprises viral genomic DNA.

* * * * *

UNITED STATES PATENT AND TRADEMARK OFFICE
CERTIFICATE OF CORRECTION

Page 1 of 1

PATENT NO. : 8,598,338 B2
APPLICATION NO. : 12/718713
DATED : December 3, 2013
INVENTOR(S) : Robert Jackson Bair et al.

It is certified that error appears in the above-identified patent and that said Letters Patent is hereby corrected as shown below:

On the Title Page

Item (56):
"Ahmad, F., "Free Energy Changes in Denaturation of Ribonuclease a by Mixed Denaturants," *The Journal of Biological Chemistry,* 259(7):4183-4186, 1984." should read, --Ahmad, F., "Free Energy Changes in Denaturation of Ribonuclease A by Mixed Denaturants," *The Journal of Biological Chemistry,* 259(7):4183-4186, 1984.--.

Item (56):
"Galinski et al., "The Kosmotropic (structure forming) Effect of Compensatory Solutes," *Comparative Biochemistry and Physiology, 117 Part A: Physiology* (3):356-365, 1997." should read, --Galinski et al., "The Kosmotropic (structure forming) Effect of Compensatory Solutes," *Comparative Biochemistry and Physiology, 117 Part A: Physiology* (3):357-365, 1997.--.

In the Claims

Column 24, Lines 35-36:
"(b) adding a DNA Spiking Solution to the biological material mixture of step" should read, --(b) adding a DNA Spiking Solution to the mixture of step (a);--.

Signed and Sealed this
Sixteenth Day of September, 2014

Michelle K. Lee
*Deputy Director of the United States Patent and Trademark Office*